United States Patent [19]

Shields

[11] Patent Number: 5,549,568
[45] Date of Patent: Aug. 27, 1996

[54] ELASTOMERIC NEEDLE SHIELD AND HUB-CAP

[76] Inventor: Jack W. Shields, 1950 Las Tunas Rd., Santa Barbara, Calif. 93103

[21] Appl. No.: 293,798

[22] Filed: Aug. 22, 1994

[51] Int. Cl.$^6$ ..................................... A61M 5/32
[52] U.S. Cl. ........................... 604/192; 604/263
[58] Field of Search .................... 604/192, 198, 604/263, 199

[56] References Cited

U.S. PATENT DOCUMENTS

| | | | |
|---|---|---|---|
| 4,316,462 | 2/1982 | Baker | 604/192 X |
| 4,735,618 | 4/1988 | Hagen | 604/192 |
| 4,915,697 | 4/1990 | DuPont | 604/192 |
| 4,964,866 | 10/1990 | Szwarc | 604/192 |
| 4,998,922 | 3/1991 | Kuracina et al. | 604/192 |
| 5,092,852 | 3/1992 | Poling | 604/192 |
| 5,122,123 | 6/1992 | Vaillancourt | 604/192 |
| 5,147,325 | 9/1992 | Mitchell et al. | 604/192 |
| 5,295,972 | 3/1994 | Mischenko | 604/192 |
| 5,312,366 | 5/1994 | Vailancourt | 604/192 |

*Primary Examiner*—John D. Yasko

[57] ABSTRACT

I describe a an elastomeric tube whose leading end holds a conical puncture-resistant needle shield and whose trailing end is attached to the conical hub of a hollow needle. A removable cylindric hub-cap initially covers the elastomeric tube surrounding the needle. The purpose of the assembly is to sustain needle sterility before use and to prevent accidental needle sticks after use for transfering fluids. The user attaches the assembly to a Luer-Lok on a syringe, on the leading end of tubing or in a pre-assembled form on a Vacutainer™ needle. He/she removes the cylindric hub-cap and inserts the needle tip into a cap on a fluid container or into a patient. The conical needle shield slides back over the shaft of the needle, while the elastomeric tube shortens like an accordion. When the user retracts the needle from the container or from a patient, elastic recoil in the tube causes the conical needle shield to slide back and automatically re-shield the tip of the needle.

2 Claims, 1 Drawing Sheet

ELASTOMERIC NEEDLE SHIELD AND HUB-CAP

FIELD OF THE INVENTION

This invention relates to the sterile protection of a hollow bore needle before use in a patient and prevention of accidental needle sticks following use. An object is to prevent contamination of the needle surface before use and finger access to the needle tip after use.

DESCRIPTION OF PRIOR ART

In order to prevent accidental needle sticks to health care workers in situations where the bore of the needle might contain blood-borne pathogens, especially viruses which cause AIDS or hepatitis, a variety of devices have been designed. Many of these do not protect the shaft of the needle from contamination by skin- water- or air-borne pathogens.

Most of the devices for protecting health care workers (HCW) from accidental needle sticks depend on sliding a puncture resistant cylinder beyond the sharp tip of a hollow-bore steel needle or pulling the needle within a cylindric holder so that access to the sharp tip is precluded. Such devices are either manually operated or provided with spring mechanisms which project the needle into a guarded position. In general, these devices leave considerable space beyond the tip of the needle because the diameter of the protective cylinder is large in comparison with the diameter of the needle. Characteristically, the diameter of the cylinder exceeds the diameter of the needle hub, of tubing trailing the needle hub or of a syringe to which the needle hub is attached. Because such devices do not depend on the use of elastomers or cones, they will not be reviewed in detail.

The use of elastomeric caps over needles is standard in Vacutainer™ systems wherein a latex cap covers the trailing end of a double-ended needle inserted into a holder. The latex cap prevents blood spillage into the holder from the trailing end of the needle, but provides no protective features for the sharp needle tip which is customarily well- protected until detachment of the needle hub from a cylindric holder for a vacuum vial.

Shields disclosed in U.S. Pat. No. 4,932,946 (Jun. 12, 1990) and in U.S. Pat. No. 5,061,250 (Oct. 29, 1991) a slit elastomeric tube attached to the hub of a needle for safely covering the needle tip by means of a cylindric guard. The needle is exposed and recovered by stretching and bending the elastic tube such that the needle passes through the slit. These disclosures are pertinent, but not applicable to the instant invention which claims no slit.

Sims disclosed in U.S. Pat. No. 4,846,809 (Apr. 11, 1989) a needle tip protective device comprising a collapsible sleeve disposed about the shank of a needle with a protective cap located at one end to enclose the sharp point of a needle. A sealing member in the device permits exposure of the needle when pushed through. The device was claimed to spring back to re-enclose the needle tip after use or to protect HCW.

Kuracina et al disclosed in U.S. Pat. No. 4,998,922 (Mar. 12, 1991) a device consisting of a needle hub-attached, spring-operated plastic tube with four longitudinal slits for safely covering and automatically recapping the tip of a hollow-bore steel needle. Lacking springs and slits, the instant invention differs structurally, although the purpose for protecting the needle tip is similar. Although surfaces between slits prevent finger contamination of the needle shaft before use, four slits might not prevent access of air- or water-borne micro-organisms.

SUMMARY OF THE INVENTION

The object of this invention is to provide a simple, efficient, inexpensive device in the form of a needle hub-attached elastomeric tube with an enclosed leading conical shield for maintaining sterility of a hollow-bore needle before use and for preventing accidental needle stick injuries from the needle tip to HCW after use.

Usage is structurally limited to syringes, Vacutainer™ systems and trailing tubing wherein needle insertion into a patient or into a container is straight in and straight out in the long axis of the hollow needle. Where needle insertion is oblique, as in venous access, use is not recommended.

DESCRIPTION OF PREFERRED EMBODIMENTS

Figure 1:
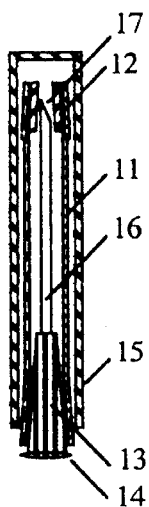
FIG. 1 is a diagrammatic coronal section in the long axis of the needle showing a needle hub-cap over the elastomeric tube and needle hub. (Scale 1:1).

As shown in FIG. 1, the device consists of an elastomeric tube 11 containing a rigid cone 12 inserted into its leading end. The small leading end of the cone 12 is almost flush with the leading end of the elastomeric tube 11 and has an external diameter nearly equal to the internal diameter of the elastomeric tube 11. The external diameter of frustum of the cone 12, being larger in diameter than the internal diameter of the elastomeric tube 11, is held by elastic recoil in the leading end of the elastomeric tube. The trailing end of the elastomeric tube 11 affixes by stretching to the leading end of a conical needle hub 13 whose external diameters are progressively greater than internal diameter of the elastomeric tube 11. Between the trailing end of the elastomeric tube 11 and trailing flanges 14 on a needle hub 13, sufficient space is left such that the over-riding elastomer will not interfere with customary flange action within a Luer-Lok (not shown). Instead of a standard conical needle sheath normally supplied with a hollow-bore steel needle, a puncture-resistant substantially cylindric needle hub-cap with a closed leading end 15 slip-connects over the elastomer covering the leading end the needle hub 13 to form an air-tight reversible connection and encloses the entire length of the elastomeric tube 11 and contents without binding.

The length of the elastomeric tube 11 is determined by the length of a hollow needle 16 exposed beyond its needle hub 13. The bore of the elastomeric tube 11 is equal to or smaller than the leading external diameter of the inserted cone 12 and smaller than the leading external diameter the conical needle hub 13. The thickness can vary with material durometer and size of the inserted cone 12. The dimensions of the inserted cone 12 depend, in turn, on the gauge of the hollow needle 16 held by the needle hub 13 and the length of the needle bevel 17.

The length of the inserted cone 12 should be approximately 1.5 times the internal diameter of the elastomeric tube and should be adjusted such that the leading tip of the needle 16 trails the leading opening by a distance at least equal to the length of the needle bevel 17. The internal diameter of the cone 12 at its leading end should be slightly larger than the external diameter of the needle and even larger at the trailing end. The external diameter of the inserted cone 12 at its leading end should be equal to or slightly greater than the internal diameter of the inserted elastomeric tube 11; and should be substantially greater at the trailing end, such that the constituent elastomer must stretch over the frustum which retards displacement in a trailing direction. The material of the inserted cone should be rigid and resistant to puncture by the sharp tip of a hollow-bore steel needle.

Figure 2:
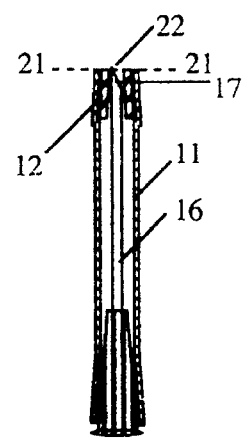
FIG. 2 is a similar section with the needle hub-cap removed and the needle advanced almost to the leading opening of the elastomeric tube.

As shown in FIG. 2, the cylindric needle hub-cap 15 has been removed and the leading end of the sterile assembly has been advanced against a flat surface depicted by a dotted line 21—21. The leading tip of the hollow needle 22 is ready to penetrate and use for giving a subcutaneous injection, for retrieving fluid from a vial with a flat cap, or for conveying fluid to or from a container with an appropriate nipple having a flat surface. It should be noted that forward movement of the needle for a distance as small as the length of the needle bevel compresses the elastomeric tube, but produces little visible distortion.

It should be noted further that the shaft 16 and level 17 of the hollow needle are covered such they can not be contaminated by touching. The sharp tip 22 of the needle 16 is recessed by a distance equal to or longer than the beveled tip and exposed through a leading aperture in the cone 12 only slightly larger than the external diameter of the needle of selected gauge.

Figure 3:
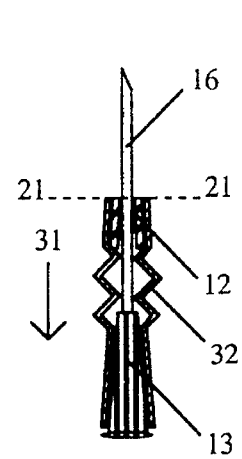
FIG. 3 is a similar section with the elastomeric tube pushed back as a result of needle entry into skin or into a container.

As shown in FIG. 3, when the leading end of the needle 16 is inserted straight through the skin, a vial cap or nipple of a container, depicted by the plane 21—21, the trailing end of the cone 12 will compress the elastomeric tube against the leading part of the needle hub in the direction of the arrow 31 such that tube assumes a shortened accordion-like shape 32. This allows the leading two-thirds of the needle 16 to be used effectively for intended purposes already described.

Figure 4:
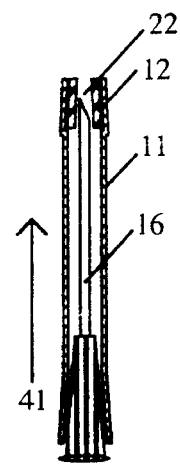
FIG. 4 is a similar section showing the elastomeric tube automatically re-extended.

As shown in FIG. 4, when the needle 16 is withdrawn from the intended site of usage, the elastomeric tube 11 will return to its original shape in the direction of the arrow 41. As a result, the leading tip 22 of the needle 16 will be re-enclosed in the cone 12. Thus, in practice, the user will find it difficult to stick himself/herself intentionally or accidentally with the leading tip of the needle.

In operation, the user employs this assembled device like a standard hub-attached hollow-bore needle with a sharp leading tip. He/she attaches the needle hub to a standard Luer-Lok or uses one pre-attached to the trailing end of a Vacutainer™ needle. After removal of the outside cylindric hub-cap from the leading end of the needle hub, everything is the same. However, the user will find it impossible to touch the needle shaft and difficult to touch the needle tip before use. After use, he/she will find the needle automatically re-shielded and simple to dispose of conveniently, either directly into a sharps container, or in a recapped condition using a single-handed approach which will be relatively safe owing to the fact that the entire needle is already re-shielded and vulnerable only to a forceful straight-on approach.

The user will find it difficult to use this device under conditions where the needle must be inserted into a receptive surface at an angle of less than 75°, unless he/she retracts the trailing end of the elastomeric tube to expose the leading end of the needle before insertion into the skin or into a container. Thus, the assembly is not recommended for intravenous access.

Figure 5:
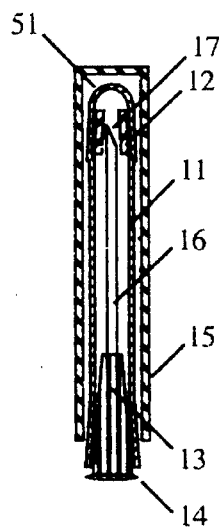
FIG. 5 is a section similar to that in FIG. 1 showing a closed leading end on the elastomeric tube.
Figure 6:
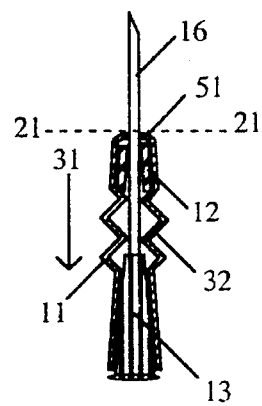
FIG. 6 is a section similar to that in FIG. 3 showing the closed leading end of the elastomeric tube under pressure from a flat surface.
Figure 7:
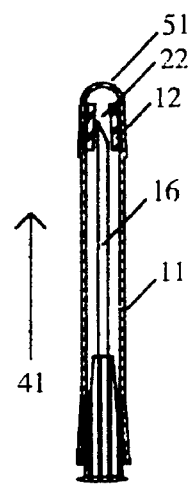
FIG. 7 is a section similar to that in FIG. 4 showing the closed leading end of the elastomeric tube after pressure has been released.

A second and preferred embodiment with a closed leading end 51 on the elastomeric tube 11 is shown in FIGS. 5–7. As shown in FIG. 5, the rigid cone 12 is inserted into the leading end of the elastomeric tube 11 to the point where the elastomer narrows in diameter to form a rounded closed end 51. Position of the needle bevel 17 in the rigid cone 12 should be as already described with a leading space approximately equal to the length of the beveled tip 17 of the needle 16 in the leading end of the rigid cone 12. It should be noted that the needle 16 within the elastomeric tube 11 can be expected to remain untouchable and sterile after the cylindric hub cap 15 is removed, because the entire leading portions of the elastomeric tube are closed.

As shown in FIG. 6, when the needle 16 penetrates a flat surface 21—21 after passing through the rounded closed end 51 of the elastomeric tube 16, the closed end 51 will be compressed against the leading end of the rigid conical needle shield 12 whose posterior displacement within the elastomeric tube 16 is prevented by its wide trailing frustum.

As shown in FIG. 7, after the needle 16 has been withdrawn from the flat surface, the rounded closed end 51 of the elastomeric tube 11 will assume its original shape and, depending on the gauge of the needle 16, seal the path of the needle throught the rounded closed end 51. Thus, leakage from the bore of the needle outside of the elastomeric tube 11 will be minimized.

This preferred version of the assembly shown in FIGS. 5–7 is more complex to manufacture, because it requires elastomeric molding, as opposed to the cutting and fitting of selected tubing. However, the advantages with respect to maintaining needle sterility before use and preventing fluid leakage after use are important considerations.

It should be mentioned that silicone is a good choice for fabrication of said elastomeric tube; while the inserted cone must be rigid and resistant to puncture by the beveled tip of a hollow needle made of stainless steel. The foregoing specifications are provided to instruct in the efficient medical use of the invention. The scope should not be limited to the specifications cited.

I claim:

1. An elastomeric needle shield for enhancing safe transfer of sterile fluids and preventing hazardous injuries from an enclosed hollow needle with a beveled tip, a shank, and a conical hub affixable to a syringe, said elastomeric needle shield comprising an elastomeric tube having:
   (a) an axial length approximately equal to the combined axial length of the beveled tip, shank and conical hub of the hollow needle,
   (b) a leading end enclosing a tubular shield with:
      i. a rigid, needle puncture-resistant consistency;
      ii. a leading end nearly flush with said leading end of said elastomeric tube;

iii. an internal diameter greater than the external diameter of the shank of the hollow needle, a leading external diameter equal to or greater than the internal diameter of said elastomeric tube, and a trailing external diameter substantially greater than the internal diameter of said elastomeric tube, such that upon axial compression of said leading end of said elastomeric tube against a penetrable surface, the hollow needle slides through to extend beyond the confines of said tubular shield held by means of elastic recoil inside said leading end of said elastomeric tube; and iv. an axial length at least 1.5 times longer than said internal diameter of said elastomeric tube and substantially shorter than the axial length of the shank of the hollow needle, and wherein the beveled tip of the hollow needle is recessed in said leading end of said tubular shield by a distance at least equal to the length of the beveled tip of the hollow needle when said elastomeric tube recoils automatically to assume its original shape on cessation of axial compression against a surface penetrable by the beveled tip and shank of the hollow needle;

(c) a body portion enclosing the shank of the hollow needle in a space with an axial length approximately equal to the axial length of the shank and an internal diameter substantially greater than the external diameter of the shank; and (d) a trailing end wherein said internal diameter of said elastomeric tube is less than the external diameter of the mid-portion of the conical hub of the hollow needle, such that said trailing end of said elastomeric tube affixes securely over the conical hub by means of elastic recoil.

2. The elastomeric needle shield, as in claim 1, wherein a second and preferred embodiment further comprises said elastomeric tube having a closed leading end stretching over said leading end of said tubular shield, said closed leading end being penetrable by the beveled tip and shank of the hollow needle, such that the hollow needle is contained in an entirely closed space before said leading end of said elastomeric tube is axially compressed against a penetrable surface to expose the beveled tip and shank of the hollow needle, and after the beveled tip of the hollow needle is automatically restored to said recessed position within said tubular shield by means of elastic recoil in said body portion of said elastomeric tube on cessation of said axial compression.

* * * * *